United States Patent
Engel

(10) Patent No.: US 11,291,614 B2
(45) Date of Patent: Apr. 5, 2022

(54) FACIAL SCRUB COMPOSITION

(71) Applicant: Alicia Engel, Indianapolis, IN (US)

(72) Inventor: Alicia Engel, Indianapolis, IN (US)

( * ) Notice: Subject to any disclaimer, the term of this patent is extended or adjusted under 35 U.S.C. 154(b) by 93 days.

(21) Appl. No.: 16/880,484

(22) Filed: May 21, 2020

(65) Prior Publication Data

US 2021/0361543 A1    Nov. 25, 2021

(51) Int. Cl.
| | |
|---|---|
| A61Q 19/10 | (2006.01) |
| A61K 8/19 | (2006.01) |
| A61K 8/34 | (2006.01) |
| A61K 8/24 | (2006.01) |
| A61K 8/368 | (2006.01) |
| A61K 8/46 | (2006.01) |
| A61K 8/49 | (2006.01) |
| A61K 8/73 | (2006.01) |
| A61K 8/86 | (2006.01) |

(52) U.S. Cl.
CPC .......... *A61K 8/19* (2013.01); *A61K 8/24* (2013.01); *A61K 8/34* (2013.01); *A61K 8/345* (2013.01); *A61K 8/368* (2013.01); *A61K 8/463* (2013.01); *A61K 8/49* (2013.01); *A61K 8/73* (2013.01); *A61K 8/86* (2013.01); *A61Q 19/10* (2013.01)

(58) Field of Classification Search
CPC ........ A61Q 10/10; A61Q 19/10; A61K 8/463; A61K 8/86; A61K 8/34; A61K 8/39; A61K 2800/48; A61K 8/73; A61K 8/368; A61K 8/49

USPC .......................................................... 510/137
See application file for complete search history.

(56) References Cited

U.S. PATENT DOCUMENTS

| | | |
|---|---|---|
| 7,101,578 B1 | 9/2006 | Revivo |
| 7,195,770 B2 | 3/2007 | Gitomer |
| 8,729,000 B2 | 5/2014 | Seidling |
| 8,921,293 B1 | 12/2014 | Eckburg |
| 2002/0086039 A1* | 7/2002 | Lee .............. C03C 3/097 424/401 |
| 2006/0093634 A1* | 5/2006 | Lutz ............. A61Q 19/00 424/401 |
| 2006/0104932 A1 | 5/2006 | Rau |
| 2007/0249514 A1* | 10/2007 | Midha ............ A61K 8/731 510/475 |
| 2009/0169500 A1* | 7/2009 | Sunkara .......... A61P 43/00 424/65 |
| 2010/0233128 A1 | 9/2010 | Panasenko |
| 2016/0038386 A1 | 2/2016 | Hoy |

FOREIGN PATENT DOCUMENTS

EP    3192490    7/2017

* cited by examiner

*Primary Examiner* — Eisa B Elhilo

(57) ABSTRACT

A facial scrub composition includes a composition that includes water, glycerin, isopropyl alcohol, tetrasodium phosphate, benzoic acid, poloxamer, sodium benzoate, sodium lauryl sulfate, sodium saccharin, xanthan gum and baking soda.

2 Claims, No Drawings

FACIAL SCRUB COMPOSITION

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to face cleaning solution and more particularly pertains to a new face cleaning solution for cleaning a person's skin such that the skin is left with a tight sensation and for the reduction of wrinkles.

(2) Description of Related Art Including Information Disclosed Under 37 CFR 1.97 and 1.98

The prior art relates to face cleaning solutions used for cleansing and skin tightening properties.

(h) BRIEF SUMMARY OF THE INVENTION

An embodiment of the disclosure meets the needs presented above by generally comprising a composition that includes water, glycerin, isopropyl alcohol, tetrasodium phosphate, benzoic acid, poloxamer, sodium benzoate, sodium lauryl sulfate, sodium saccharin, xanthan gum and baking soda.

In another embodiment, the composition comprises glycerin, isopropyl alcohol, benzoic acid, poloxamer, sodium benzoate, sodium lauryl sulfate, baking soda, wherein the baking soda comprises between 75% and 85% of a weight of said composition.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

Not Applicable

(j) DETAILED DESCRIPTION OF THE INVENTION

A new face cleaning solution embodying the principles and concepts of an embodiment of the disclosure will now be described.

The facial scrub composition generally comprises a mixture of components that is applied to a person's skin and in particular to the face of a user of the composition. The components of the composition include:

2% to 6% water;
2% to 6% glycerin ($C_3H_8O3$);
0.5% to 2% of 8.7% isopropyl alcohol ($C_3H_8O$);
0.5% to 2% tetrasodium phosphate ($Na_4O_7P_2$);
0.5% to 2% benzoic acid ($C_7H_6O_2$);
0.5% to 2% poloxamer 407 ($HO(C_2H_4O)_a(C_3H_6O)_b(C_2H_4O)H$;
0.5% to 2% sodium benzoate ($C_7H_5NaO_2$);
0.5% to 2% sodium lauryl sulfate ($NaC_{12}H_{25}SO_4$);
0.5% to 2% sodium saccharin ($C_7H_5NO_3S$);
0.5% to 2% xanthan gum ($C_{35}H_{49}O_{29}$); and
75% to 85% baking soda (sodium bicarbonate $NaHCO_3$).

In one specific embodiment, the composition consists of:

4% water;
4% glycerin ($C_3H_8O3$);
1% of 8.7% isopropyl alcohol ($C_3H_8O$);
1% tetrasodium phosphate ($Na_4O_7P_2$);
1% benzoic acid ($C_7H_6O_2$);
1% poloxamer 407 ($HO(C_2H_4O)_a(C_3H_6O)_b(C_2H_4O)H$;
1% sodium benzoate ($C_7H_5NaO_2$);
1% sodium lauryl sulfate ($NaC_{12}H_{25}SO_4$);
1% sodium saccharin ($C_7H_5NO_3S$);
1% xanthan gum ($C_{35}H_{49}O_{29}$);
2% mint or other organic extract or oil for scent;
2% FDC Blue No. 1, or other coloring agent;
1% FD&C Yellow No. 5, or other coloring agent; and
79% baking soda (sodium bicarbonate $NaHCO_3$).

In use, the composition is applied to the face and neck of the user and rubbed against the skin. The composition is then washed off with water and the face dried.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A composition for cleaning for a person's skin, said composition comprising by volume:
   2% to 6% water;
   2% to 6% glycerin;
   0.5% to 2% of 8.7% isopropyl alcohol;
   0.5% to 2% tetrasodium phosphate;
   0.5% to 2% benzoic acid;
   5% to 2% poloxamer 407;
   0.5% to 2% sodium benzoate;
   0.5% to 2% sodium lauryl sulfate;
   0.5% to 2% sodium saccharin;
   0.5% to 2% xanthan gum; and
   75% to 85% baking soda.

2. A composition for cleaning for a person's skin, said composition comprising:
   glycerin;
   isopropyl alcohol;
   benzoic acid;
   poloxamer;
   sodium benzoate;
   sodium lauryl sulfate; and
   baking soda, wherein said baking soda comprises between 75% and 85% of a weight of said composition.

* * * * *